United States Patent
Wise et al.

(10) Patent No.: US 6,270,489 B1
(45) Date of Patent: Aug. 7, 2001

(54) ANTI-CLOTTING METHODS AND APPARATUS FOR INDWELLING CATHETER TUBES

(75) Inventors: Marcia A. Wise, Draper; H. Robert Moorehead, Salt Lake City, both of UT (US)

(73) Assignee: Catheter Innovations, Inc., Salt Lake City, UT (US)

( * ) Notice: Subject to any disclaimer, the term of this patent is extended or adjusted under 35 U.S.C. 154(b) by 0 days.

(21) Appl. No.: 09/648,718

(22) Filed: Aug. 25, 2000

Related U.S. Application Data

(62) Division of application No. 09/345,892, filed on Jul. 1, 1999.

(51) Int. Cl.[7] .................................................. A61M 31/00
(52) U.S. Cl. ............................................ 604/508; 604/509
(58) Field of Search ........................... 608/508, 101.01, 608/101.02, 101.04, 101.05, 28, 4.01

(56) References Cited

U.S. PATENT DOCUMENTS

| | | | |
|---|---|---|---|
| 4,771,777 | * | 9/1988 | Horzewski et al. ................. 606/194 |
| 5,403,274 | * | 4/1995 | Cannon ..................................... 604/9 |
| 5,713,854 | * | 2/1998 | Inderbitzen et al. ................... 604/53 |
| 5,792,118 | | 8/1998 | Kurth et al. .......................... 604/246 |
| 5,807,331 | * | 9/1998 | Heijer et al. ......................... 604/101 |
| 5,833,650 | * | 11/1998 | Imran ..................................... 604/96 |
| 5,843,027 | * | 12/1998 | Stone et al. ............................. 604/96 |
| 5,855,563 | * | 1/1999 | Kaplan et al. ........................ 600/439 |
| 5,868,719 | * | 2/1999 | Tsukernik .............................. 604/265 |
| 5,902,266 | * | 5/1999 | Leone et al. ............................ 604/96 |
| 5,916,193 | * | 6/1999 | Stevens et al. ......................... 604/53 |

* cited by examiner

*Primary Examiner*—Richard K. Seidel
*Assistant Examiner*—Kevin C. Sirmons
(74) *Attorney, Agent, or Firm*—Foster & Foster

(57) ABSTRACT

Enabled or activated closure and sealing devices in the form of closure balloons, and related methods, are disclosed, which substantially preclude entry and clotting of blood at the distal end of a lumen of an indwelling catheter tube during times when flow therein is not occurring. The closure and sealing balloon is disabled or deactivated to accommodate flow, without clotting, through the lumen of the catheter tube when flow therein is resumed.

13 Claims, 4 Drawing Sheets

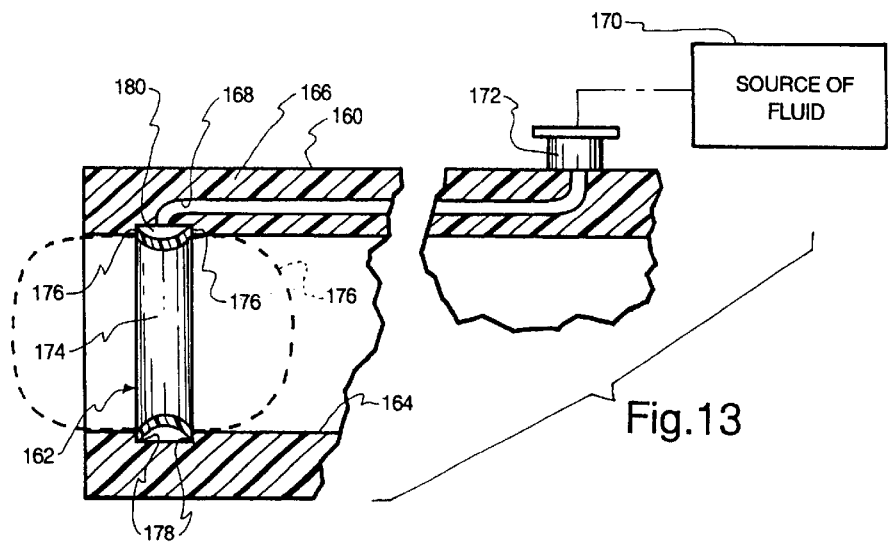
Fig.13
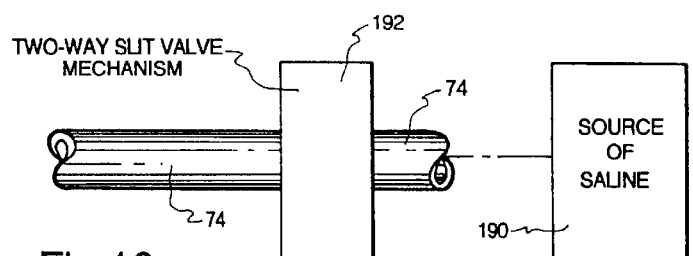
Fig.16
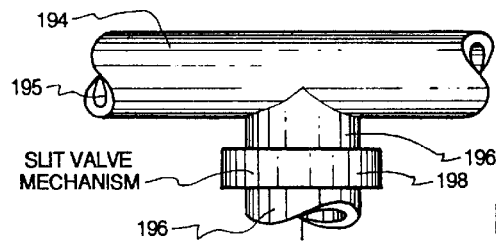
Fig.17
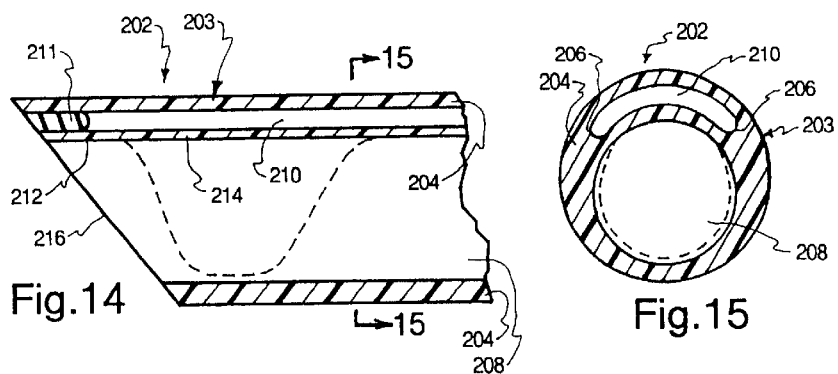
Fig.14
Fig.15

ANTI-CLOTTING METHODS AND APPARATUS FOR INDWELLING CATHETER TUBES

CONTINUITY

This application is a division of our copending U.S. patent application Ser. No. 09/345,892 filed Jul. 1, 1999.

FIELD OF THE INVENTION

The present invention relates generally to catheter tubes and more specifically to anti-clotting methods and apparatus for catheter tubes.

BACKGROUND

Typically, for example only, many dialysis medical patients are treated for a few hours every two or three days. Dialysis is performed by removing blood from the patient through an effluent or egress catheter tube, processing the removed blood through an artificial kidney machine to filter impurities from the blood, and returning the cleansed or processed blood to the patient through an influent, infusion or ingress catheter tube. The two catheter tubes may be any of several configurations, including but not limited to two essentially separate catheter tubes, a dual lumen catheter or any other suitable egress/ingress arrangement.

It is desirable to limit the number of times a vessel of the patient is penetrated for placement therein of dialysis catheter tubes. Accordingly, once placed, it is desirable for the distal end of the egress and ingress catheter tubes to be left indwelling for an extended period of time to accommodate spaced, repeated dialysis. Accordingly, the indwelling egress and ingress catheter tubes are inactive typically for much longer intervals than they are active. In addition, catheter tubes for other purposes are sometimes left indwelling for long periods of time and are frequently idle with no flow therethrough. This includes, but is not limited to, the central venous catheter category.

During idle times, when flow is not occurring in a given indwelling catheter tube, blood tends to enter the distal opening of the indwelling catheter tube. This is true even when the lumen of the catheter tube is full of liquid, other than blood, such as saline or heparin. During these idle times, blood flow through the vessel around the outside of the catheter tube tends to evacuate liquid from the lumen at the distal tip of the idle indwelling catheter tube, which is replaced by blood. This blood in the distal tip of each catheter tube tends to remain stationary, risking the development of a clot.

When clotting occurs within the lumen at the distal end of a catheter tube, an expensive clotbusting medication, such as Urokinase, is introduced into the proximal end of the catheter tube. After a suitable waiting period, during which the clot is softened, the medication and softened clot are aspirated from the catheter tube through the proximal end thereof. Where sufficient softening does not occur, the expensive clot-busting medication process may be repeated. Sometimes the clot is discharged into the vessel from the lumen using a liquid under positive pressure, which creates undesired risks for the patient. If all else fails, the catheter tube with the clot therein is removed from the patient at the vessel puncture site and a new replacement catheter tube inserted into the vessel.

Given the foregoing, provision of reliable and inexpensive methods and apparatus for avoiding or greatly alleviating clotting in indwelling catheter tubes would solve a long standing medical problem.

BRIEF SUMMARY AND OBJECTS OF THE PRESENT INVENTION

In brief summary, the present invention overcomes or substantially alleviates clotting problems heretofore associated with certain types of catheter tubes. The present invention utilizes an enabled or activated closure and sealing device and related methods to substantially preclude entry and clotting of blood at the distal end of a lumen of an indwelling catheter tube during times when flow therein is not occurring. The closure and sealing device is disabled or deactivated to accommodate flow, without clotting, through the lumen of the catheter tube when flow therein is initiated or resumed. In a presently preferred form, the closure device may comprise an inflatable/deflatable balloon, which, when inflated, closes the lumen of the catheter tube at the distal end thereof. The invention can be configured to accommodate flushing or purging of the lumen of the indwelling catheter tube either before or after inflated deployment of the balloon closure. The balloon mechanism may be inserted into the patient as the catheter tube is inserted, with the balloon either inflated or deflated; or separately after the catheter tube is first inserted. The invention applies to trimmable and non-trimmable catheters. The balloon may be a separate component or integrated with the catheter tube. Slit valve mechanisms may be used to control flow through the lumen of the catheter tube, to prevent or alleviate leakage at the proximal end of the catheter tube, and to control fluid flow to and from the balloon.

In view of the foregoing, it is a primary object of the present invention to overcome or materially alleviate clotting problems heretofore associated with certain types of catheter tubes.

Another important object is the provision of anti-clotting methods and apparatus for indwelling catheter tubes.

A further paramount object is the utilization of a closure and sealing device and related methods which, when the device is activated, substantially precludes entry and clotting of blood at the distal end of a lumen of an indwelling catheter tube during times when flow therein is not occurring and/or when the catheter tube and balloon are collectively introduced into the vessel.

Another dominant object is the provision of a closure and sealing device and related methods, which device can be activated to preclude entry and clotting of blood within a lumen of a catheter tube during introduction and/or during times when flow therein is not occurring and can be deactivated to accommodate flow through the lumen of the catheter tube.

It is another valuable object of the present invention to provide an inflatable/deflatable balloon device for selective closure of a lumen of a catheter tube at the distal end thereof, when inflated.

An additional significant object is the provision of a trimmable or non-trimmable catheter tube in combination with a balloon closure device at the distal end of the catheter tube which accommodates use of a liquid under pressure to flush or purge the lumen of the indwelling catheter tube, either before or after inflated deployment of the balloon closure.

A further valued object is the provision of novel balloon closures in combination with the distal ends of catheter tubes wherein a slit valve mechanism is used to control flow through the lumen of an associated catheter tube, to prevent or alleviate leakage at the proximal end of the catheter tube, and/or to control fluid flow to and from the balloon.

These and other objects and features of the present invention will be apparent from the detailed description taken with reference to the accompanying drawings.

BRIEF DESCRIPTION OF THE DRAWINGS

FIG. 13 is an enlarged cross section of the distal end of a catheter tube equipped with an integrated balloon closure;

FIG. 14 is an enlarged fragmentary cross section of the distal end of a catheter tube equipped with another form of integrated balloon closure;

FIG. 15 is a cross section taken along lines 15—15 of FIG. 14;

FIG. 16 is a fragmentary diagrammatic illustration of a slit valve mechanism used to control inflation and deflation of a balloon closure at the distal end of a catheter tube; and FIG. 17 is a fragmentary diagrammatic illustration of a slit valve mechanism used to control purging of the lumen of a catheter tube.

DETAILED DESCRIPTION OF THE ILLUSTRATED EMBODIMENTS

Figure 1:
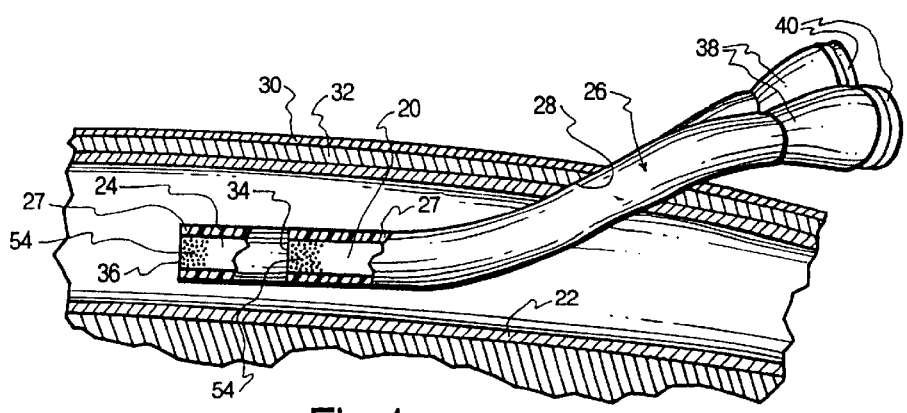
FIGS. 1 and 2 are elevational views partly in cross section of the prior art dialysis catheter tubes, illustrating blood clots within the lumen of each tube at the distal end thereof.

Reference is now made in detail to the drawings wherein like numerals are used to designate like parts throughout. In reference to FIGS. 1 and 2, which relate to a problem associated with the prior art. Specifically, catheters of various kinds, including but not limited to central venous catheters and dialysis catheters are idle for substantial intervals of time. That is to say, flow of liquid through catheter tubes of the type mentioned, is discontinued for extended periods of time and thereafter resumed. In the case of dialysis, blood is removed from the patient through an effluent or egress catheter lumen 20 and is processed through an artificial kidney machine to filter impurities from the blood. The processed blood is then returned to the vessel through an ingress catheter lumen 24. See FIGS. 1 and 2. In FIG. 1, the egress and ingress lumens 20 and 24 comprise part of the dual lumen catheter, generally designated 26, the dual lumen catheter 26 passing through a venepuncture site 28, which penetrates through the skin 30, tissue 32 and vessel wall 22 as such that the distal ends 34 and 36 of the dual lumen catheter tube comprising lumens 20 and 24 are indwelling, while two proximal fittings or hubs 38 are outdwelling and are illustrated as being closed, in each case, by a removable stopper or plug 40.

Figure 2:
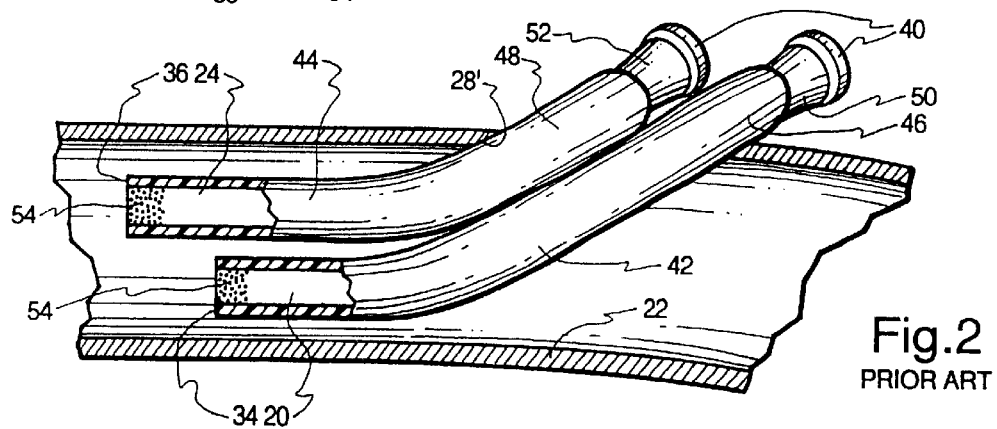

In FIG. 2, side by side catheter tubes 42 and 44 pass through a common venepuncture site 28', defining, respectively, lumens 20 and 24. Catheter tubes 42 and 44 comprise distal ends 34 and 36, respectively. The exposed proximal ends 46 and 48 of the catheter tubes 42 and 44 are respectively equipped with hubs 50 and 52, each of which is illustrated as being closed by a stopper or plug 40. While not shown, sometimes a single lumen catheter is also left indwelling for substantial intervals when flow is not occurring through the lumen thereof. Because it is desirable to limit the number of times a vessel of a patient is punctured or penetrated for placement therein of one or more desired catheter tubes, catheter tubes which are used only intermittently are retained indwelling so long as there is sufficient medical reason not to remove the same and replace them with other catheters.

During the interval of time when a catheter or a plurality of catheters are left indwelling in a vessel, with no flow occurring through the catheter or catheters, blood tends to enter the distal end of each catheter tube, i.e., in the case of FIGS. 1 and 2 at the distal portions of lumens 20 and 24. This is true even when the lumen or lumens are full of liquid, other than blood, such as saline or heparin. During these idle times, blood flow through the vessel around the outside of the catheter tube or tubes tends to evacuate liquid from the lumen or lumens at the distal tip or tips and to replace such evacuated liquid by blood. Because such blood at the distal tip of a catheter lumen tends to remain stationary, clots within the lumen or lumens can and sometimes do develop. These clots are identified by the numeral 54 in FIGS. 1 and 2.

When clotting occurs within a lumen at the distal end of a catheter tube, an expensive clotbusting medication, such as Urokinase, is sometimes introduced into the proximal end of the catheter tube. After a suitable waiting period, during which the clot is softened, the medication and softened clot are aspirated from the catheter tube through the proximal end thereof. When sufficient softening does not occur, the expensive clot-busting medication process may be repeated. Sometimes the clot is discharged into the vessel from the lumen using a liquid under positive pressure, which creates undesired risks for the patient. If all else fails, the catheter tube with the clot therein is removed from the patient at the vessel puncture site and a new replacement catheter is inserted into the vessel.

Figure 3:
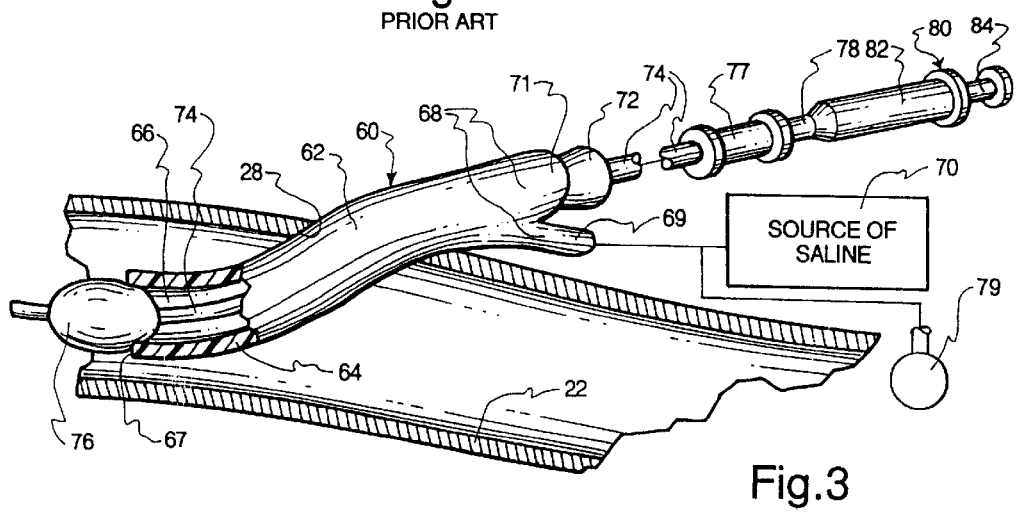
FIG. 3 is an elevational view partly in cross section of one configuration of the present invention comprising a balloon end closure sealing the lumen of a catheter tube at the distal end thereof.

Given the foregoing, it should be clear that avoidance of a clot at the distal end of an indwelling catheter tube would be a far better solution than trying to deal with a clot once it has developed. The present invention overcomes or substantially alleviates clotting problems heretofore associated with certain types of catheter tubes. One embodiment of the present invention is illustrated in FIG. 3 and is generally designated as 60. The catheter assembly 60 comprises a catheter tube 62, having a hollow cylindrical wall 64 defining a lumen 66 therein. The distal end 67 of the catheter tube 62 is indwelling within vessel 22. The outdwelling portion of the catheter tube 62 comprises a Y-adapter 68. One branch 69 of the adapter is connected to a source 70 of saline which is or can be placed under pressure. The Y-adapter 69 can be part of the catheter, but in certain applications can preferably be part of the balloon closure assembly as explained hereinafter in greater detail.

The main, straight proximal end 71 of the Y-adapter at 68 connects to a proximal fitting or hub 72, which comprises an internal seal through which a hollow stem 74 passes. Stem 74 is in fluid communication with an internal balloon 76 and an external indicator balloon 79. The stem 74 connects across a hollow fitting 77 which comprises a Luer fitting into which a syringe, generally designated 80, is inserted. Syringe 80 comprises a barrel 82 and a plunger 84. The amount of saline in the barrel 82 of the syringe is that required to fully inflate the balloon 76. For example, saline may be initially loaded into the barrel 82 of the syringe 80 and, upon placement of the balloon 76, in deflated condition, at the distal end 67 of the catheter tube 62, the plunger 84 is advanced to discharge saline under pressure from the barrel 82 across the Luer fitting 78, across hollow fitting 77, along hollow stem 74 to inflate the balloon 76 into the configuration illustrated in FIG. 3. The Luer fitting 78, as is conventional, comprises a seal which prevents leakage both when free of the syringe 80 and when connected to the syringe. Likewise, the saline from source 70 inflates the indicator balloon 79. When balloon 79 is fully inflated, the medical technician or other user knows the internal balloon 76 is fully inflated. Furthermore, the indicator balloon 79 is constructed so that it will rupture due to excessive pressure before the balloon 76 ruptures, to insure safety in use. Also, after placement and before inflation of the balloon 76, saline or other appropriate liquid may be displaced under pressure through port 69 to purge passageway 66 of any undesired substances, such as blood or other infusant that may have been used.

The balloon 76 and the catheter tube 62 are preserved in the relationship illustrated in FIG. 3 until such time as it is desired to resume flow through the catheter tube 62, in which case the balloon 76 is deflated by aspirating saline from balloon 76 into the barrel 82. The balloon 76, in a deflated condition, may be left near the distal end 67 of the catheter tube 62 and infusion of a suitable fluid through the catheter is accomplished by connection of the fluid source to the arm 69. In the alternative, the balloon 76 may be withdrawn from the catheter tube, which would entail removal of the stop 72, the deflated balloon 76, the balloon stem 74, the fitting 77, the Luer fitting 78 and the syringe 80 and, thereafter, connection of the proximal end of the main bore of the catheter tube to other apparatus which accommodates liquid flow through the lumen 66, in or out as appropriate.

Figure 4:
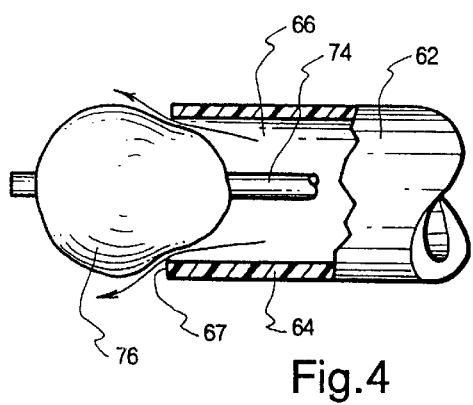
FIG. 4 is an enlarged fragmentary view partly in cross section of the balloon closure of FIG. 3 unsealed from the interior wall of the catheter tube by flushing or purging liquid under pressure.
Figure 5:
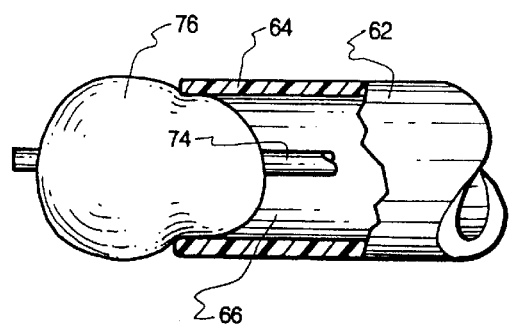
FIG. 5 is a view similar to FIG. 4 showing the balloon closure resealed after displacement of purging liquid under pressure is discontinued.

With the balloon 76 inflated, as illustrated in FIG. 3, blood is not permitted to back-flow into the lumen 66 and, therefore, clotting within the distal end of lumen 66 is avoided. Nevertheless, at one or more appropriate times, saline from source 70 may be delivered under pressure to the lumen 66 to purge the lumen, which will temporarily dislodge and unseal the balloon 76 from the catheter tube 62, essentially as shown in FIG. 4. Once the delivery of saline under pressure from source 70 is discontinued, the balloon 76 will resume its closed, sealed and anti-clotting position, as illustrated in FIG. 5.

Figure 7:
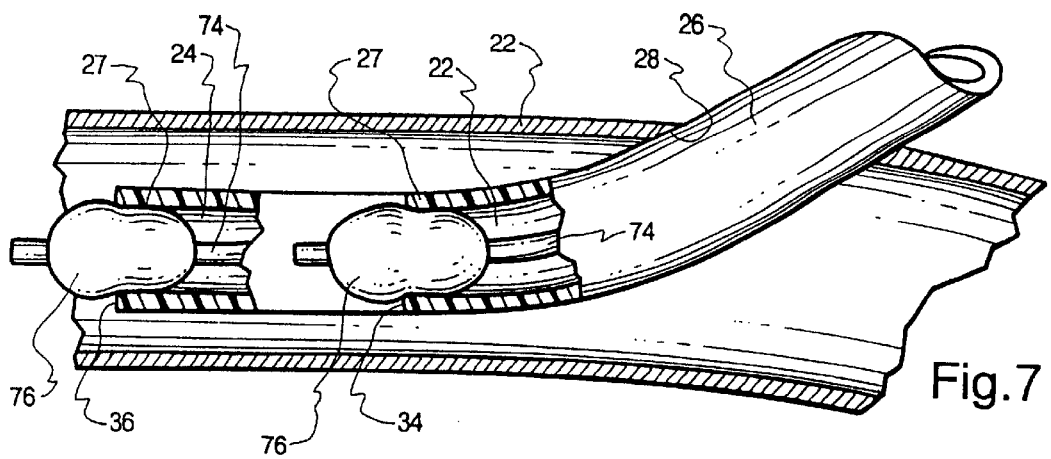
FIGS. 6, 7 and 8 are elevational views partly in cross section of balloon closure in combination with various catheter tubes.

When the anti-clotting embodiment shown and described in connection with FIG. 3 is used on a dual lumen catheter assembly, of the type illustrated in FIG. 1, two balloon mechanisms are used of the type described in connection with FIG. 3, one for each lumen 20 and 24. This anti-clotting arrangement is illustrated in FIG. 7, which is numerated consistent with the numerals used in FIGS. 1 and 3, so far as applicable.

Figure 8:
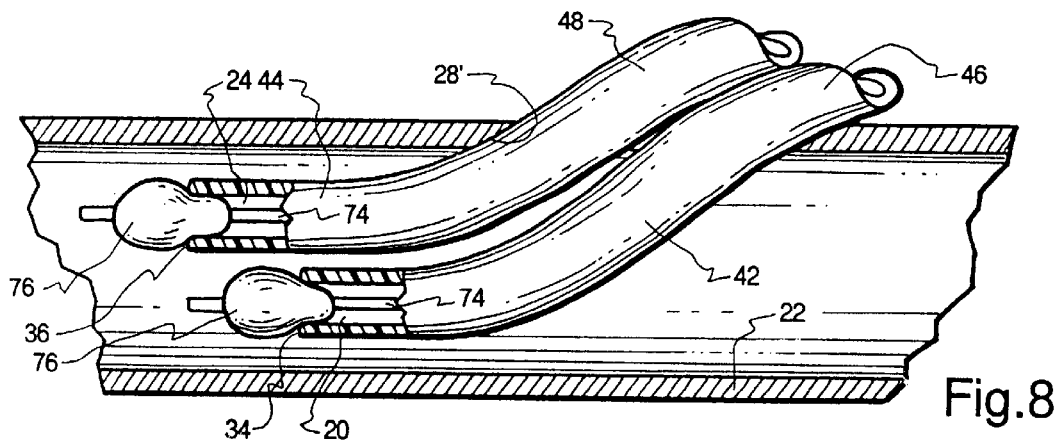

Similarly, when two catheters are used, of the type shown in FIG. 2, the anti-clotting embodiment of FIG. 3 may be combined therewith in the manner illustrated in FIG. 8, which has been enumerated so as to conform to the enumeration of FIGS. 2 and 3, so far as applicable.

Figure 6:
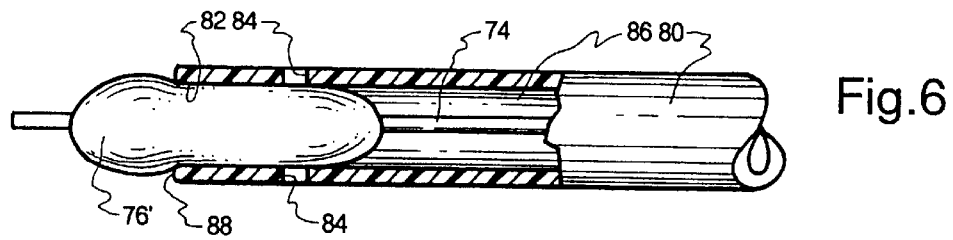

In reference to FIG. 6, it is understood by those skilled in the art that some catheters, including catheter tube 80, comprise not only a distal end opening 82, but one or more side ports 84. To prevent entry of blood through one or more ports 84 during times when the catheter tube 80 is not being actively used, an elongated balloon 76' is provided so that, when inflated, the balloon 76' not only closes and seals the catheter tube lumen 86 adjacent the distal end 88 of the catheter tube 80, but also closes each side port 84 to prevent entry of blood therethrough.

It is to be understood that the present invention applies to trimmable catheters including but not limited to peripherally inserted central catheters (PICC) and to tunnel catheters. These catheters are characterized as being trimmable because the length thereof is custom sized to the anatomy of a specific patient to equal the distance between the entry site and the desired location of the distal end of the catheter tube. Typically, this desired length or distance is measured with a ruler along but outside the patient. The measured distance is transferred to the catheter tube and the catheter tube is cut (trimmed) to the desired length.

After the catheter tube is so trimmed, the present invention may be implemented by inserting balloon closure (obturator) and stem into the catheter tube while outside the body. The distal end of the balloon closure is placed adjacent to the distal end of the catheter tube and locked in this position. Then the catheter tube and balloon with stem may be simultaneously inserted into a vessel of the patient until the distal end of the catheter tube is correctly positioned in the patient.

In the alternative, the locked stem, with proximal hub and balloon may be removed from the catheter tube while it is external of the patient and the catheter tube by itself inserted through a puncture site into the vessel and advanced until the distal end thereof is correctly positioned in the patient. Thereafter the balloon and stem may be inserted into the indwelling catheter tube until the hub associated with the stem is seated as sealed within the hub or proximal fitting of the catheter tube, which will correctly position the balloon adjacent to the distal end of the catheter tube.

Blood leakage through the proximal fitting of the catheter may be prevented by use of a slit valve within the proximal fitting, or minimized by manually collapsing the proximal portion of the catheter tube or placement of the user's thumb over the proximal end, so far as possible.

The present invention also applies to non-trimmable catheter tubes as exemplarily explained herein.

From the foregoing, it is clear that the present invention utilizes an enabled or activated closure and sealing device, and practices related methods, to substantially preclude entry and clotting of blood at the distal end of a lumen of an indwelling catheter tube during times when flow through the catheter tube is not occurring. The closure and sealing device is disabled or deactivated to accommodate resumption of flow, without clotting, through the lumen of the catheter tube. The closure device may comprise an inflatable/deflatable balloon which, when inflated, closes the lumen of the catheter tube at the distal end thereof. The invention may be configured to accommodate flushing of the lumen of the catheter tube either before or after inflated deployment of the balloon closure.

With reference to FIGS. 9 through 12, a Touhy-Borst fitting may be used in conjunction with the present invention to deliver and remove saline under pressure to and from the balloon closure 76 and to deliver saline or other liquid under pressure through the associated catheter tube to purge the interior thereof. More specifically, in reference to FIG. 9, the outdwelling trailing end of a catheter tube 100 is illustrated, where the distal end of the catheter tube 100 is indwelling within a vessel of a patient. Within the catheter tube 100 is disposed the balloon inflating stem 74 described above. The catheter tube 100 merges with a female proximal fitting or hub 102, which is connected in liquid-communicating relation with a proximal fitting 104, the interior of which comprises a hollow passageway. Fitting 104 comprises a distal male portion 106, which is press-fit into the hub 102 and a proximal hollow tube 108. The distal end of the tube 108 terminates in threads 110. See FIG. 10.

Threads 110 are threaded into a distal female threaded receptacle 112 of a hollow Tee piece, generally designated 114. The Tee piece 114 comprises a proximal portion 11 6, which is hollow, and a side port 118 and a hub 119, both of which are also hollow. Liquid flow under pressure to purge the lumen of the catheter 100 is introduced via side port 118 and passes through the hollow fitting 112, the hollow of tube 108, the hollow of fitting 104, the hollow of tube 106 and the hollow of the hub 102 to the lumen of the catheter tube 100. This may be done, for example, by placing the distal tip of a syringe, generally designated 120, into liquid-communicating relation with the hub or sealing Luer fitting 119 of port 118 with the barrel 122 of the syringe 120, when the barrel 122 is full of a suitable solution, such as saline, and advancing the plunger 124 to extrude or discharge the saline from the barrel 122 under pressure along the path mentioned above. The Luer fittings 78 and 119 may comprise a commercially available Halkey-Roberts or equivalent valve which opens upon reception of the distal end of the syringe 80 or 120 and which closes automatically when the syringe is removed. Such valves are commonly used on endotracheal tubes and Foley catheters.

Within the hollow interior 126 of the exteriorly threaded proximal connector 116 is disposed an annular seal 128 of silicone rubber or the like, which comprises a central bore or aperture 130, a distal face 132, a proximal face 134 and an annular edge face 136. As can be seen best in FIGS. 11 and 12, the annular or disc-shaped seal 128 is snugly positioned within the hollow 126, with the distal face 132 continuously abutting shoulders 138 and 140.

Figures 11, 12:
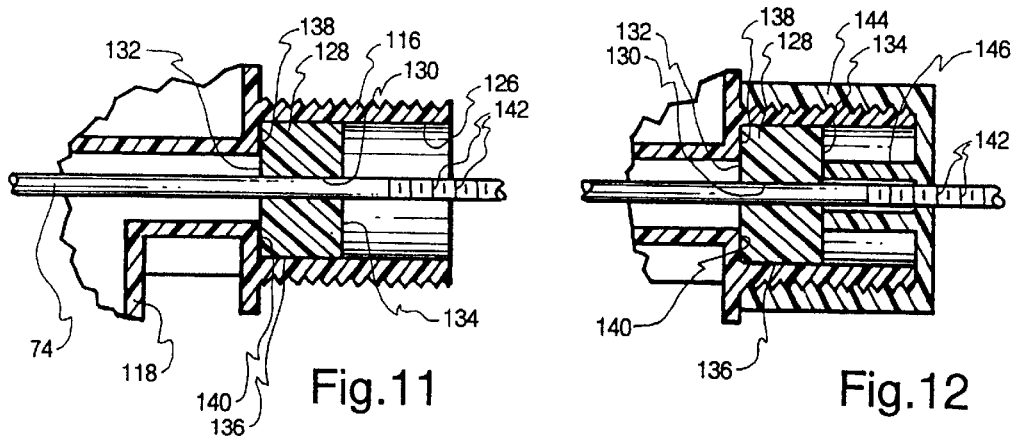
FIGS. 11 and 12 are enlarged fragmentary cross sections of a seal and clamp arrangement at the proximal end of the catheter tube of FIG. 9 through which a stem for inflating a balloon closure passes in sealed and clamped relationships respectively, the stem having distance indicia by which the balloon closure is accurately located inside the lumen at the distal end of the catheter tube.

As viewed in FIG. 11, the balloon stem 74 passes snugly but moveably through the aperture or bore 130 in the seal 128. The stem 74 is illustrated as having distance indicia 142 disposed thereon for accurate placement of the balloon at the distal end of the stem 74 directly adjacent the distal end of the catheter tube 100 while the distal end is indwelling. While distance indicia 142 is referenced to the distal internal balloon 76 and may extend from the distal balloon 76 to the proximal region of the stem 74, in most if not all applications marks 142 are needed only for an appropriate length along a proximal portion of the stem 74 sufficient to allow proper placement of the balloon 76 at the distal end of both trimmable and non-trimmable catheter tubes as determined by those skilled in the art.

However, when a double wall cap 144 is threaded upon proximal connector 116, an internal annular portion 146 compresses the annular seal 128 at surface 134. The overall effect of the compression caused by the internal annular portion 146 causes the seal 128 to attempt to expand radially outwardly and radially inwardly. This places sufficient pressure from the seal 128 upon the exterior surface of the stem 74 passing through the seal 128 so that the stem 74 can no longer be moved in either a forward or reverse direction in respect to the seal 128. In other words, the seal 128, responsive to the compaction caused by portion 146, clamps against the stem 74 causing it to be held in a desired position. In this way, the balloon at the distal end of the stem 74 is retained in its selected position directly adjacent the distal tip of the catheter tube 100 to function as an anti-clotting closure device which prohibits blood from entering into the distal end of the catheter tube lumen. See FIG. 12.

Figure 9:
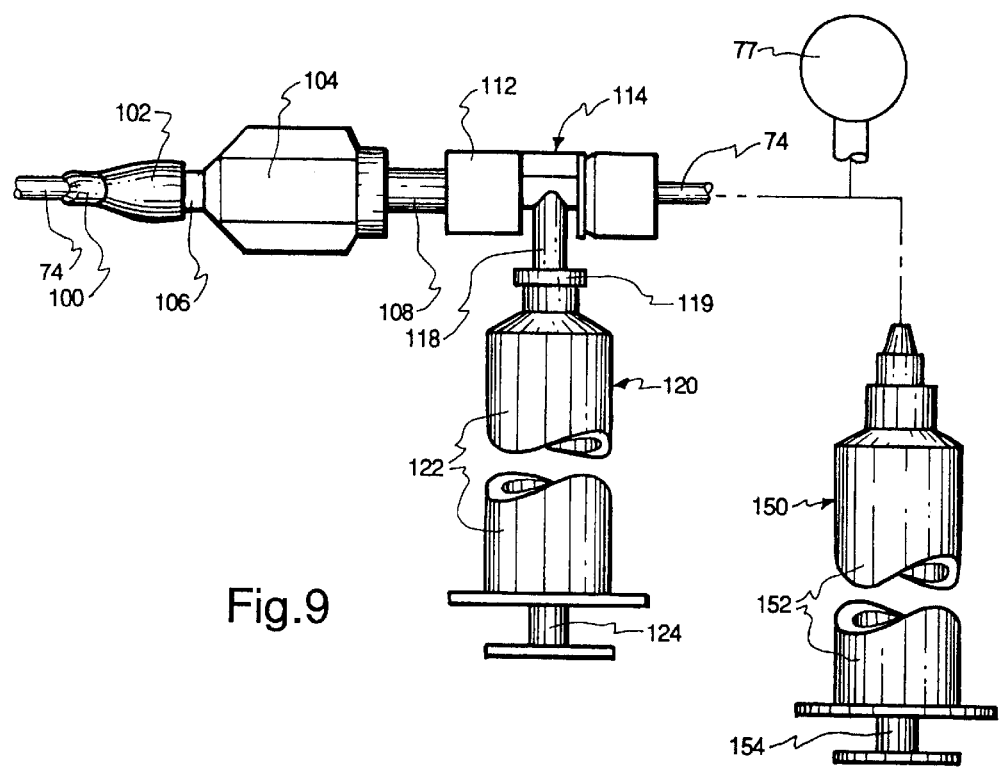
FIG. 9 is a plan view illustrating structure by which (1) flushing liquid under pressure is displaced through the lumen of a catheter tube and (2) fluid is displaced to inflate and deflate a balloon closure at the distal end of the catheter tube.
Figure 10:
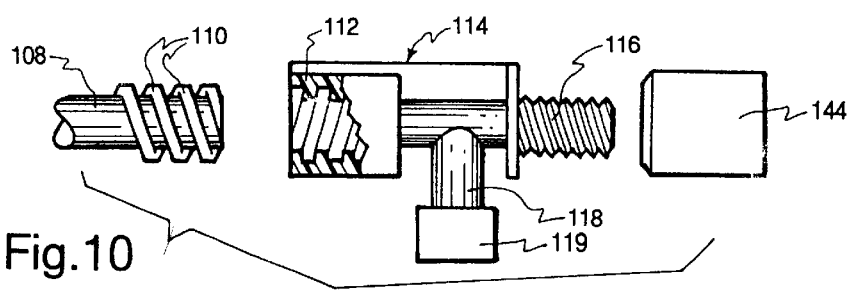
FIG. 10 is an enlarged exploded fragmentary plan view partly in cross section of the assembly at the proximal end of the catheter tube of FIG. 9.

In further reference to FIG. 9, there is illustrated a second syringe, generally designated 150, which comprises a barrel 152 initially loaded with a liquid, such as saline. The syringe 150 also comprises a plunger 154. When the plunger 154 is advanced, the liquid within the barrel 152 is discharged under pressure into and along the hollow stem 74 to inflate the closure balloon at the distal end of the catheter tube 100 to close and seal the distal end of the catheter tube. Thus, the balloon is inflated. When the plunger 154 is thereafter retracted, the liquid in the balloon is aspirated along the hollow stem 74 into the barrel 150, thereby deflating the balloon.

Reference is now made to FIG. 13, which illustrates a catheter tube 160 equipped with an integral balloon closure device, generally designated 162, for closing and sealing the distal end of the catheter tube 160 to prevent entry of blood during periods when flow is not occurring within the lumen 164 of the catheter tube, thereby preventing clotting of the blood within the lumen 164. The catheter tube 160 comprises a wall 166 which is illustrated as having a uniform thickness throughout and uniform inside and outside diameters as well. Within the wall 160 is defined a passageway 168 through which a suitable fluid, such as saline liquid, is displaced from and to a source 170. Source 170 may be a syringe of satisfactory capacity.

The source 170 communicates through a fitting 172 to the passageway 168 to inflate the balloon 162 and from the interior of the balloon through the passageway 168 and the fitting 172 to the source 170 to deflate the balloon 162. The balloon 162 comprises a rounded bladder 174, the edges 176 of which are secured to and sealed against shoulders 178, using a suitable bonding agent or the like. Shoulders 178 form two of the three walls of an annular groove 180 into which fluid under pressure is delivered to inflate the bladder 174, displacing the bladder 174 from the solid line position to the dotted line position shown in FIG. 13. When it is desired to deflate the bladder 174, the source 170 applies a negative or aspirating pressure to the fluid, evacuating the fluid from the groove 180 and passageway 168 to the source 170. Thus, the embodiment illustrated in FIG. 13 provides an integrated catheter tube and distal end closure device version of the present invention.

Reference is now made to FIGS. 14 and 15, which illustrate a further catheter with integral balloon embodiment of the present invention, generally designated 202. Catheter 202 comprises a catheter tube 203 comprising a one piece wall 204. The wall 204 is bifurcated at locations 206 (FIG. 15) to define a large central lumen 208, through which blood or other liquid is intended to flow, and a small eccentric lumen 210, through which saline, air or other fluid under pressure is displaced to inflate and deflate a closure balloon, as more fully explained hereinafter. The distal end of the lumen 210 is closed by a plug 211 or other suitable structure.

A relatively thin membrane 212 spans internally between the bifurcation points 206. A distal portion 214 of the membrane 212 is preferably weakened or of reduced strength so that fluid under pressure expands the weakened portion 214 of the membrane 212 from the solid to the dotted position, as shown in FIG. 14 and 15. When the fluid pressure is removed, the memory of the portion 214 causes it to resume its solid line position, accommodating liquid flow through the central lumen 208.

Weakening of the portion 214 may be in any known way, such as chemical treatment, reduced thickness or the like.

By having a beveled distal edge 216, the catheter tube 204 provides very little space for blood to be introduced at the distal end of the catheter tube 204, when the weakened balloon portion 214 is inflated into the dotted line position. See FIG. 14.

The foregoing description of apparatus and methods emphasizes prevention of refluxing of blood into a catheter tube, when not in use, and prevention of diffusion of blood along with the contents within the catheter, also when not in use. Some important aspects of this invention are summarized below.

Basically, a flexible tube or balloon stem with a Luer fitting on the proximal end and a balloon on the distal end which is normally in the shape of an inflated balloon is used. The balloon may be deflated by attaching a syringe to the luer fitting and aspirating the air or other fluid out of the balloon. The balloon may be so collapsed sufficiently to advance the balloon and tube or stem into the catheter tube until the balloon is at the distal end of the catheter tube. The syringe can either be disconnected and allow the balloon to resume its normal shape (conforming to the shape of the central lumen of the catheter tube into which it has been placed) or the syringe can be activated to reintroduce the air or other fluid which had been previously removed. Upon removal of the syringe, any excess air or fluid which had been instilled in the system would be dispelled from the balloon catheter through the luer fitting, at which time a cap may be placed on the luer fitting.

In respect to one method of placing a balloon at the distal tip of catheter tube, the balloon is advanced during placement until it is known that the balloon is slightly beyond tip of catheter tube, either by knowing the exact length of catheter tube and observing the measurement marks inscribed on the stem or it will be advanced until upon release of negative pressure in the stem, which collapses the balloon, it is noted that there is no resistance to movement of the balloon and stem. Without a syringe or cap on the proximal end of the stem, the stem will be moved outward (retrograde) until resistance is felt and with another one-half centimeter or so outward movement the balloon will be in the correct position in the catheter tube.

It is often desirable to use a locking mechanism such as a Touhy Borst adapter to insure that the stem does not move once it is in the desired position.

Reference is now made to FIG. 16, which illustrates a further embodiment of the present invention by which saline or other suitable fluid under pressure is discharged from and received at source 190, which may be a syringe. The saline or the like flows bi-directionally through the stem 74 to and from a balloon closure at the indwelling distal end of a catheter tube to prevent entry of blood into the tube and subsequent clotting thereof. Flow to the balloon inflates the balloon, while flow from the balloon to the source 190 deflates the balloon. FIG. 16 illustrates that a two-way slit valve mechanism 192 is positioned along the length of the tube 74. The two-way slit valve mechanism comprises a slit valve which is normally closed. Thus, a certain pressure differential to cross the slit valve is necessary in order to cause inflating or deflating fluid flow across the mechanism 192. Such slit valve mechanisms are known in the medical field. See, for example, U.S. Pat. Nos. 5,169,393, 5,201,722, and 5,205,834.

Likewise, in reference to FIG. 17, a catheter tube 194 may comprise a side port 196 equipped with a slit valve mechanism 198 similar or identical to the slit valve mechanism 192 mentioned above. Thus, saline or like liquid under pressure may be delivered from source 200 to the slit valve mechanism 198. When a suitable pressure differential threshold is reached, the slit valve within the mechanism 198 opens and the liquid under pressure proceeds into the lumen 195 of the catheter tube 194 to purge the interior of the catheter tube 194, either before or after inflating of a balloon closure at the distal end of the catheter tube for the purpose of preventing clotting of blood at the distal end of the catheter tube.

The invention may be embodied in other specific forms without departing from the spirit of the central characteristics thereof. The present embodiments therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method of addressing the problem of clotting in an idle catheter tube indwelling within a vessel of a medical patient comprising the acts of:

advancing a deflated balloon along an entirely unobstructed hollow interior of the idle indwelling catheter tube to a dismal end thereof;

inflating the balloon to entirely fill the hollow interior and contiguously engage, close, seal and occlude the entire hollow interior at the distal end of the idle indwelling catheter tube to deny blood access to the hollow interior;

purging the hollow interior of the catheter tube across a slit valve in a proximal-to-distal direction into the vessel by deforming the balloon with a suitable liquid under pressure.

2. A method according to claim 1 further comprising the act of deflating the previously inflated balloon across a slit valve.

3. A method of addressing the problem of clotting in an unobstructed idle catheter tube indwelling within a vessel of a medical patient comprising the acts of:

advancing a deflated balloon along an entirely hollow and unobstructed lumen of the idle indwelling catheter tube to a distal end thereof;

inflating the balloon across a slit valve to span the entire lumen and contiguously engage, close, seal and occlude the entire lumen at the distal end of the idle indwelling catheter tube to prevent blood infiltration and clotting by denying blood access to the entirely occluded lumen.

4. A method of addressing the problem of clotting in idle ingress and egress companion unobstructed catheter tubes indwelling within a vessel of a medical patient, comprising the acts of:

advancing a deflated balloon along an entirely hollow and unobstructed lumen of each idle ingress and egress catheter tube to a distal end of each;

inflating the respective balloons to span the entire lumen and contiguously engage, close, seal and occlude the entire lumen at the distal end of each catheter tube, thereby preventing blood infiltration and clotting by denying blood access to the entire occluded lumen of each catheter tube;

purging the hollow interior of one of both catheter tubes in a proximal-to-distal direction across a slit valve and into the vessel by deforming the balloon with a suitable liquid under pressure.

5. A method of addressing the problem of clotting in idle ingress and egress companion catheter tubes indwelling within a vessel of a medical patient, comprising the acts of:

advancing a deflated balloon along a hollow interior of each idle ingress and egress catheter tube to a distal end of each;

inflating the respective balloons to close and seal the hollow interior at the distal end of each catheter tube, thereby denying blood access to the hollow interior of each;

deflating both balloons across a slit valve and causing ingress and egress flow through the respective hollow interiors of the catheter tubes.

6. A method of addressing the problem of clotting in idle ingress and egress companion catheter tubes indwelling within a vessel of a medical patient, comprising the acts of:

advancing a deflated balloon along a hollow interior of each idle ingress and egress catheter tube to a distal end of each;

inflating the respective balloons across a slit valve to close and seal the hollow interior at the distal end of each catheter tube, thereby denying blood access to the hollow interior of each.

7. A method of addressing the problem of clotting in a catheter tube indwelling within a vessel of a patient comprising the acts of:

terminating flow along an entirely hollow unobstructed interior passageway of the indwelling catheter tube;

after the terminating act, inflating a balloon to expand the balloon across the entire interior passageway and contiguously engage, close, seal and occlude the entire hollow cross section of the interior passageway at a distal end of the indwelling catheter tube to deny blood in the vessel access to the hollow interior passageway;

purging the hollow interior of the catheter tube across a slit valve in a proximal-to-distal direction with a suitable liquid under pressure.

8. A method of addressing the problem of clotting in an entirely unobstructed catheter tube indwelling within a vessel of a patient comprising the acts of:

terminating flow along an entirely hollow unobstructed interior passageway of the indwelling catheter tube;

after the terminating act, inflating a balloon to expand the balloon across the entire interior passageway and contiguously engage, close, seal and occlude the entire hollow cross section of the interior passageway at a distal end of the indwelling catheter tube to deny blood in the vessel access to the hollow interior passageway;

deflating the balloon across a slit valve and causing flow through the hollow interior passageway of the catheter tube across the slit valve.

9. A method of addressing the problem of clotting in a catheter tube indwelling within a vessel of a patient comprising the acts of:

terminating flow along an entirely hollow unobstructed interior passageway of the indwelling catheter tube;

after the terminating act, inflating across a slit valve a balloon to expand the balloon across the entire interior passageway and contiguously engage, close, seal and occlude the entire hollow cross section of the interior passageway at a distal end of the indwelling catheter tube to deny blood in the vessel access to the hollow interior of the catheter tube.

10. A method of addressing the problem of clotting in ingress and egress companion catheter tubes indwelling within a vessel of a medical patient, comprising the acts of:

terminating ingress and egress flow along unobstructed hollow interior passageways of the indwelling catheter tubes, respectively;

after the terminating step, inflating balloons so that each balloon spans the entire interior passageway of the associated catheter tube occluding the same by engageing, closing and sealing the respective hollow interior passageways at the distal ends of the indwelling ingress and egress catheter tubes to prevent clogging within either catheter tube by denying blood in the vessel access to the hollow interior passageways;

purging one or both hollow interior passageways in a proximal-to-distal direction across a slit valve with a suitable liquid under pressure.

11. A method of addressing the problem of clotting in ingress and egress companion catheter tubes indwelling within a vessel of a medical patient, comprising the acts of:

terminating ingress and egress flow along hollow entirely unobstructed interior passageways of the indwelling catheter tubes, respectively;

after the terminating step, inflating balloons to span laterally across all of the cross section of each unobstructed passageway to engage, close and seal the respective hollow interior passageways at the distal ends of the indwelling ingress and egress catheter tubes to deny blood in the vessel access to the hollow interior passageways;

deflating the balloons and causing ingress and egress flow across a slit valve through the hollow interior passageways, respectively.

12. A method of addressing the problem of clotting in ingress and egress companion side-by-side catheter tubes indwelling within a vessel of a medical patient, comprising the acts of:

terminating ingress and egress flow along entirely unobstructed side-by-side hollow interior passageways of the indwelling side-by-side catheter tubes, respectively;

after the terminating step, inflating balloons across a slit valve to entirely fill both passageways to close and seal the respective hollow interior passageways at the distal ends of the indwelling ingress and egress catheter tubes to deny blood in the vessel access to the hollow interior passageways.

13. In combination, companion side-by-side ingress and egress catheter tubes for selective flow through a hollow passageway in each catheter tube respectively to and from the patient and a balloon associated with each catheter to accommodating selective inflation of the balloons to span cross sectional the entirety of both passageways to entirely close and seal the two hollow passageways at respective distal ends of the ingress and egress catheter tubes against entry of blood from a vessel of the patient when flow is not occurring through the hollow passageways.

* * * * *